(12) United States Patent
Degnan, III et al.

(10) Patent No.: US 10,474,970 B2
(45) Date of Patent: *Nov. 12, 2019

(54) METHODS AND APPARATUS FOR ADAPTIVE MULTISENSOR ANALISIS AND AGGREGATION

(71) Applicants: John James Degnan, III, Annapolis, MD (US); Jacobo Marcos Sirota, Takoma Park, MD (US); Kathleen Marie Fitzsimmons, Edgewater, MD (US); Christopher Treadwell Field, Baltimore, MD (US); Miodrag Cekic, Bethesda, MD (US)

(72) Inventors: John James Degnan, III, Annapolis, MD (US); Jacobo Marcos Sirota, Takoma Park, MD (US); Kathleen Marie Fitzsimmons, Edgewater, MD (US); Christopher Treadwell Field, Baltimore, MD (US); Miodrag Cekic, Bethesda, MD (US)

(73) Assignee: Sigma Space Commercial Holdings LLC, Lanham, MD (US)

(*) Notice: Subject to any disclaimer, the term of this patent is extended or adjusted under 35 U.S.C. 154(b) by 397 days.

This patent is subject to a terminal disclaimer.

(21) Appl. No.: 15/139,578

(22) Filed: Apr. 27, 2016

(65) Prior Publication Data
US 2016/0253604 A1    Sep. 1, 2016

Related U.S. Application Data

(63) Continuation-in-part of application No. 13/944,082, filed on Jul. 17, 2013, now Pat. No. 9,349,148.

(51) Int. Cl.
*G01N 21/17*    (2006.01)
*G06Q 10/06*    (2012.01)
(Continued)

(52) U.S. Cl.
CPC ........ *G06Q 10/0631* (2013.01); *G01S 7/4817* (2013.01); *G01S 17/89* (2013.01); *G06K 9/00657* (2013.01); *G06Q 10/067* (2013.01); *G06Q 40/00* (2013.01); *G06Q 50/02* (2013.01); *G01N 21/33* (2013.01); *G01N 21/35* (2013.01); *G01N 2021/1797* (2013.01); *G01N 2033/245* (2013.01); *G01S 13/86* (2013.01); *G01S 13/89* (2013.01); *G06K 2009/00644* (2013.01)

(58) Field of Classification Search
CPC .. G01N 2033/245; G01N 21/33; G01N 21/35; G01S 13/86; G01S 13/89; G01S 17/89; G06Q 40/00; G06Q 50/02
USPC ......................................................... 342/52
See application file for complete search history.

(56) References Cited

U.S. PATENT DOCUMENTS 9,349,148 B2 *   5/2016   Sirota .................... G06Q 50/02
2014/0163772 A1 * 6/2014   Vian ..................... G05D 1/0094
                                                                  701/2

* cited by examiner

*Primary Examiner* — Timothy A Brainard
(74) *Attorney, Agent, or Firm* — Miodrag Cekic

(57) ABSTRACT

The present invention is directed to a self consistent system for generation and adaptive implementation of overflying multi sensor measurements and derivation of actionable aggregants pertinent to determination of status and proactive management models of distributed resource. The system includes at least one set of calibrated overflying multisensor detectors arranged for detecting signals from electromagnetic radiation redirected by a plurality of underlying structures having a combination of features having variable scale lengths.

17 Claims, 14 Drawing Sheets

(51) Int. Cl.
G01S 17/89 (2006.01)
G06K 9/00 (2006.01)
G06Q 50/02 (2012.01)
G06Q 40/00 (2012.01)
G01S 7/481 (2006.01)
*G01N 21/33* (2006.01)
*G01N 21/35* (2014.01)
*G01S 13/86* (2006.01)
*G01S 13/89* (2006.01)
*G01N 33/24* (2006.01)

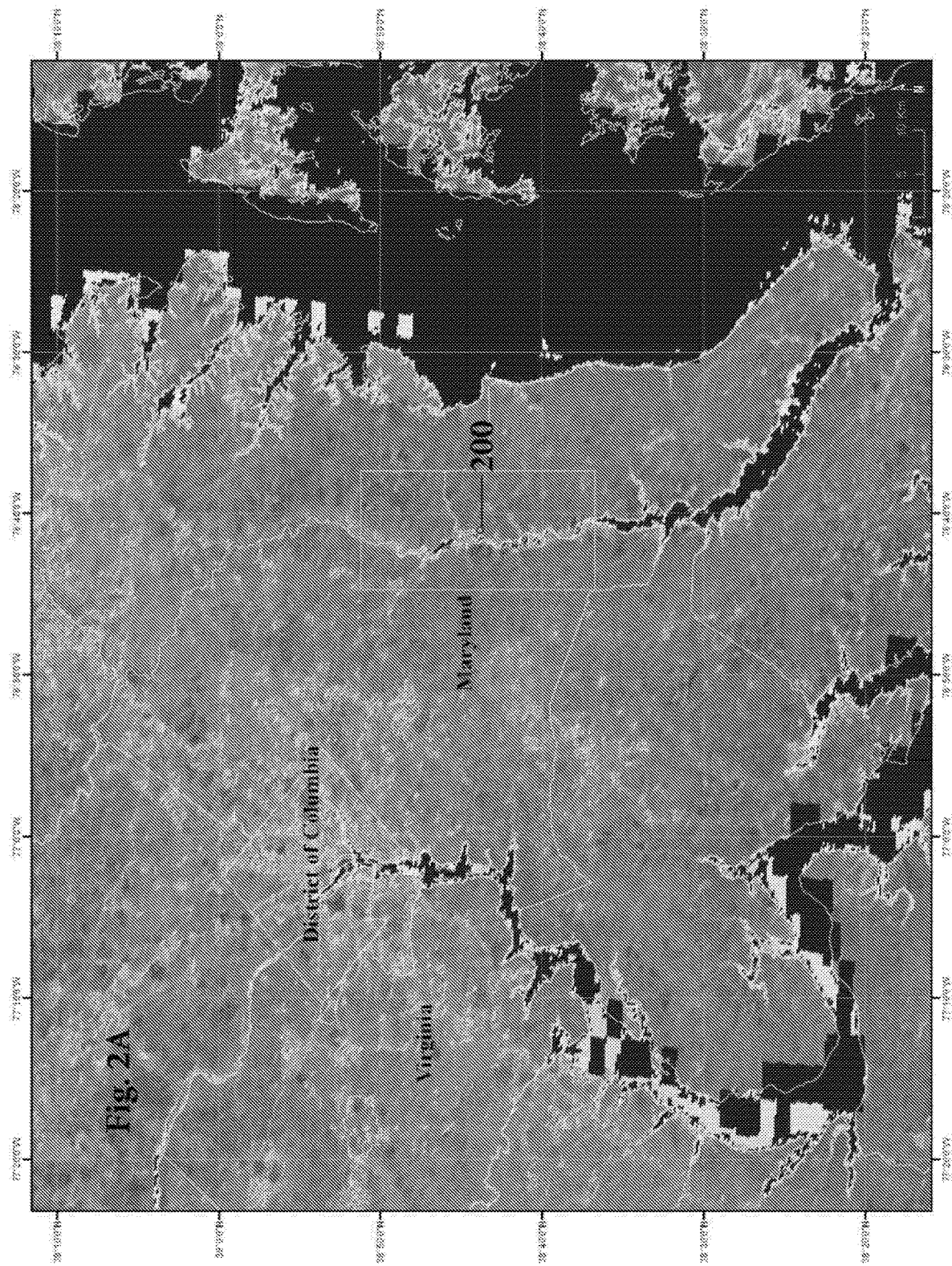

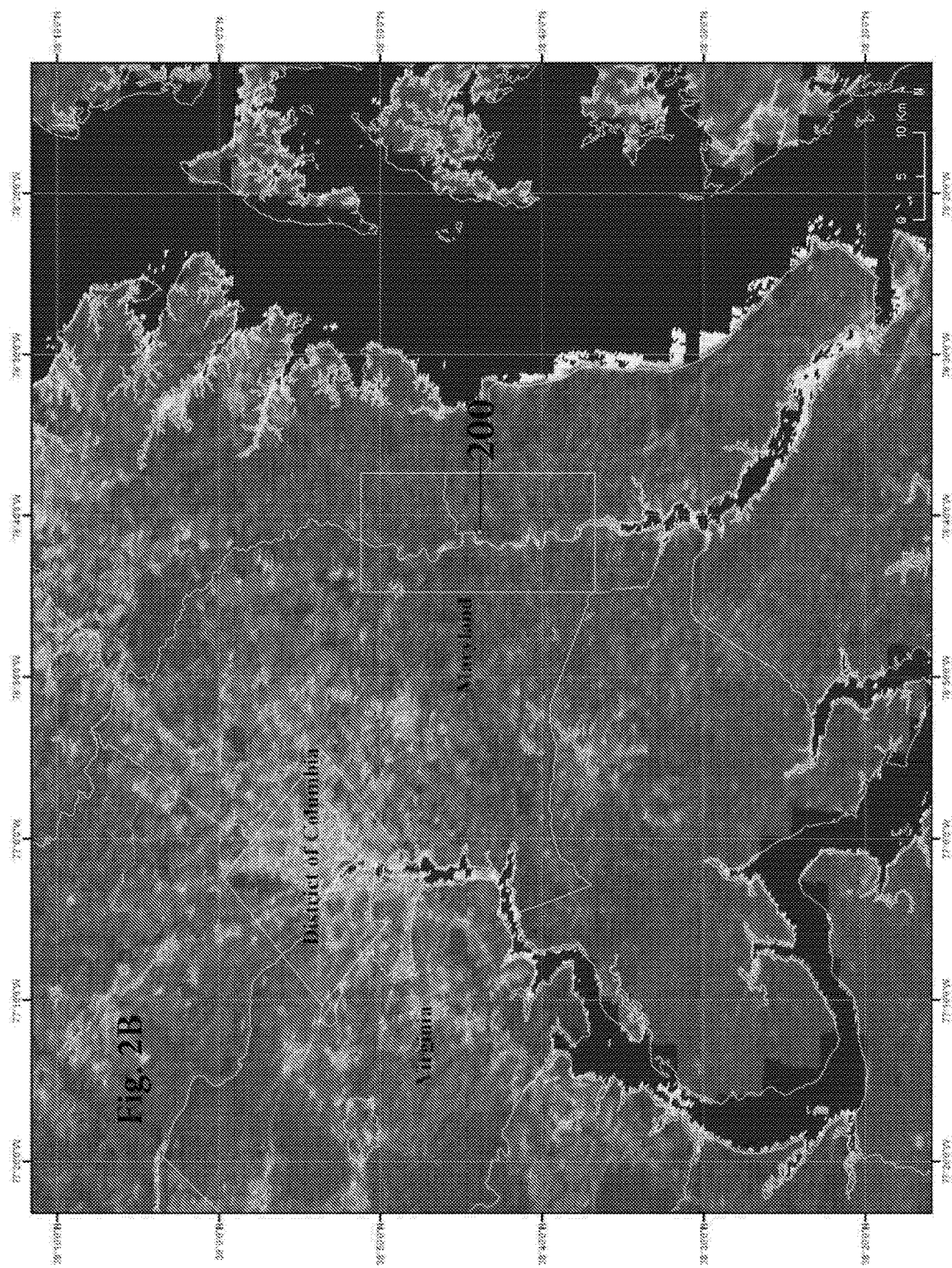

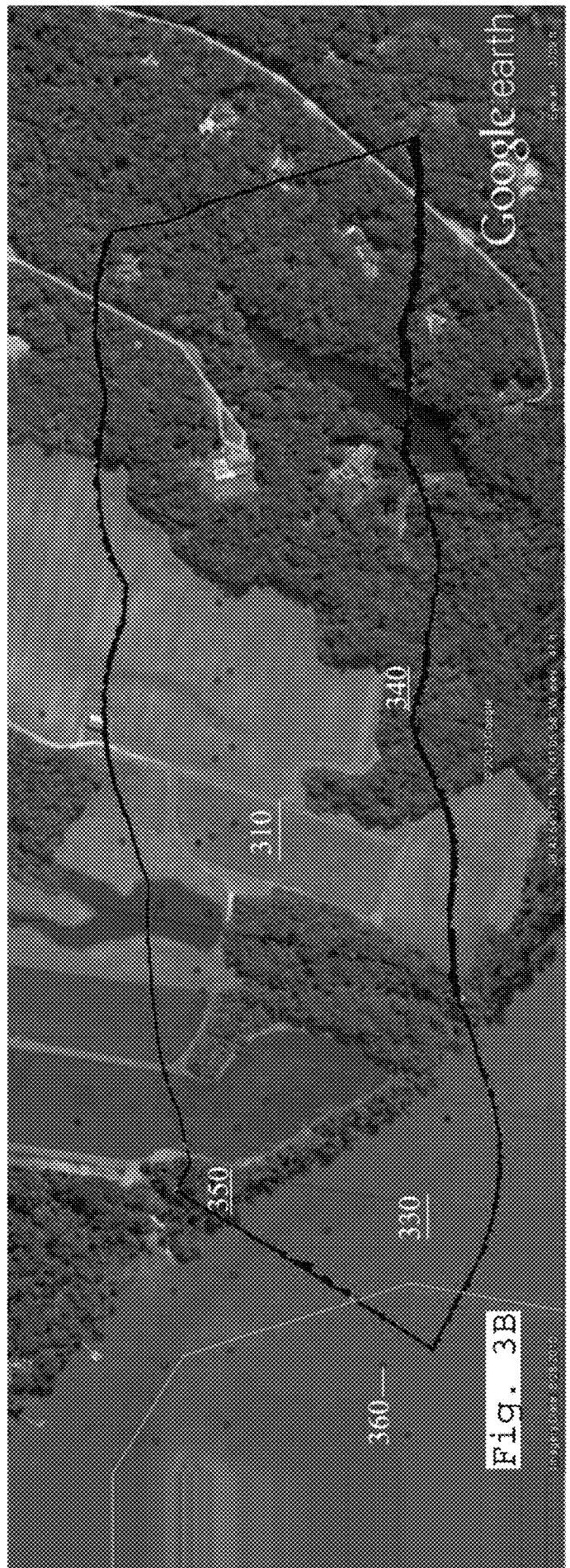

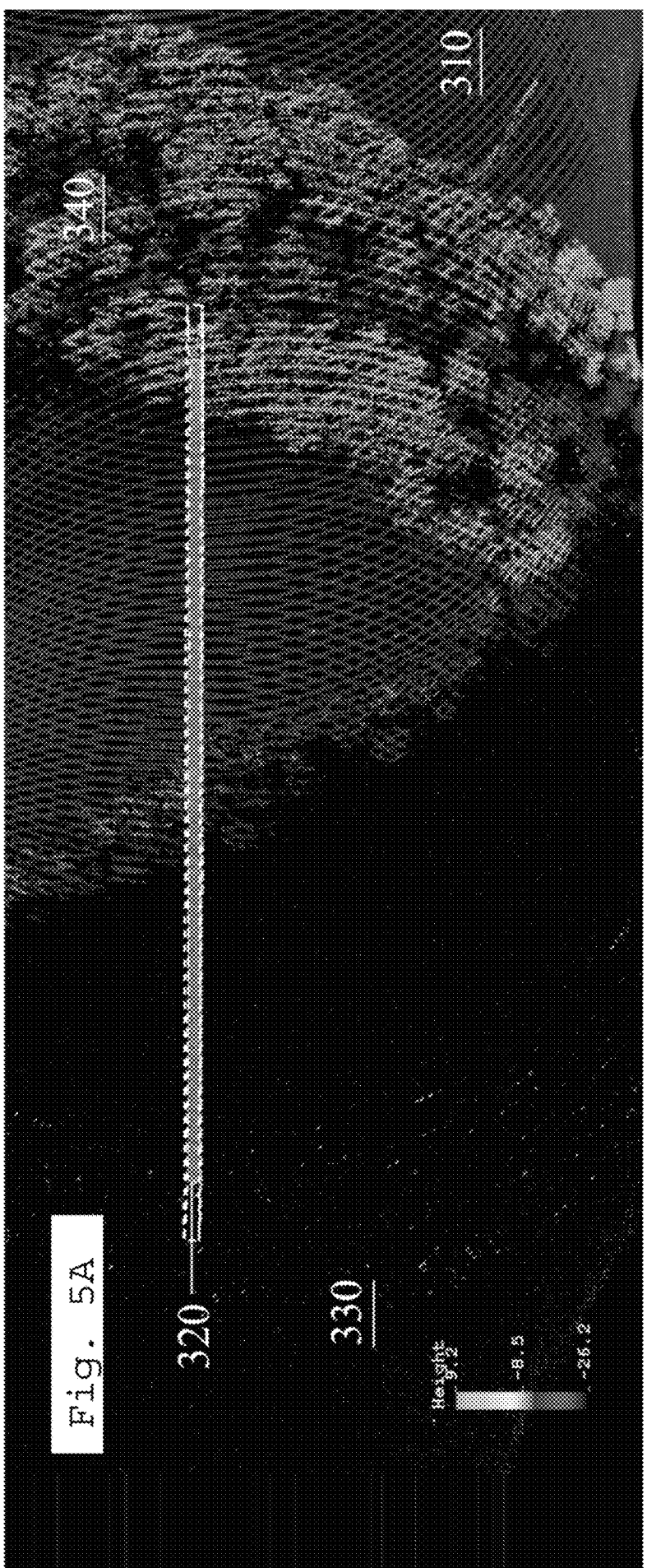

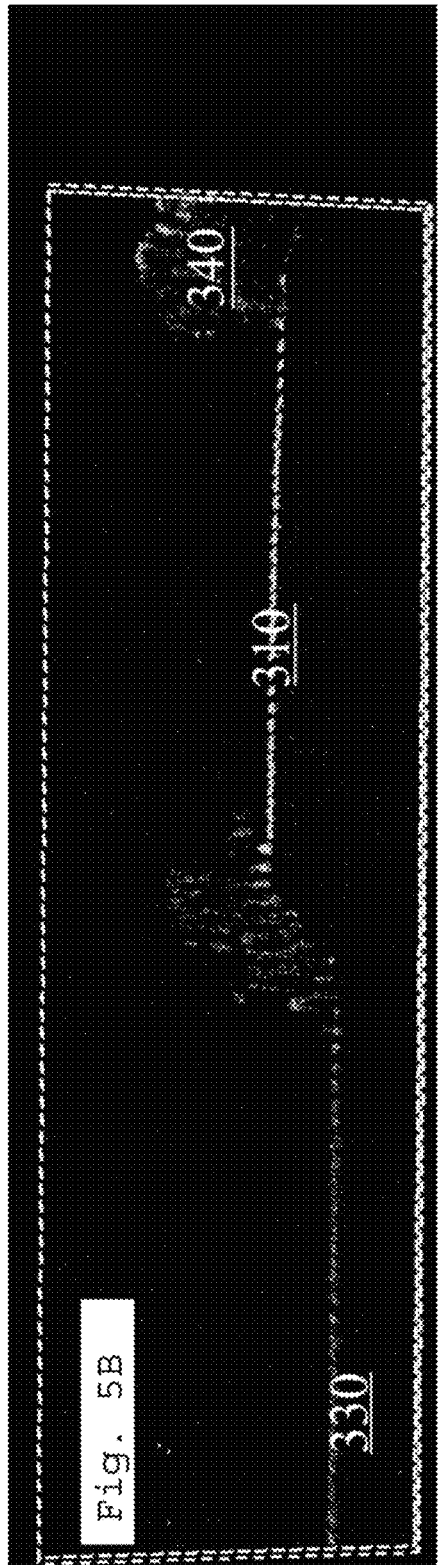

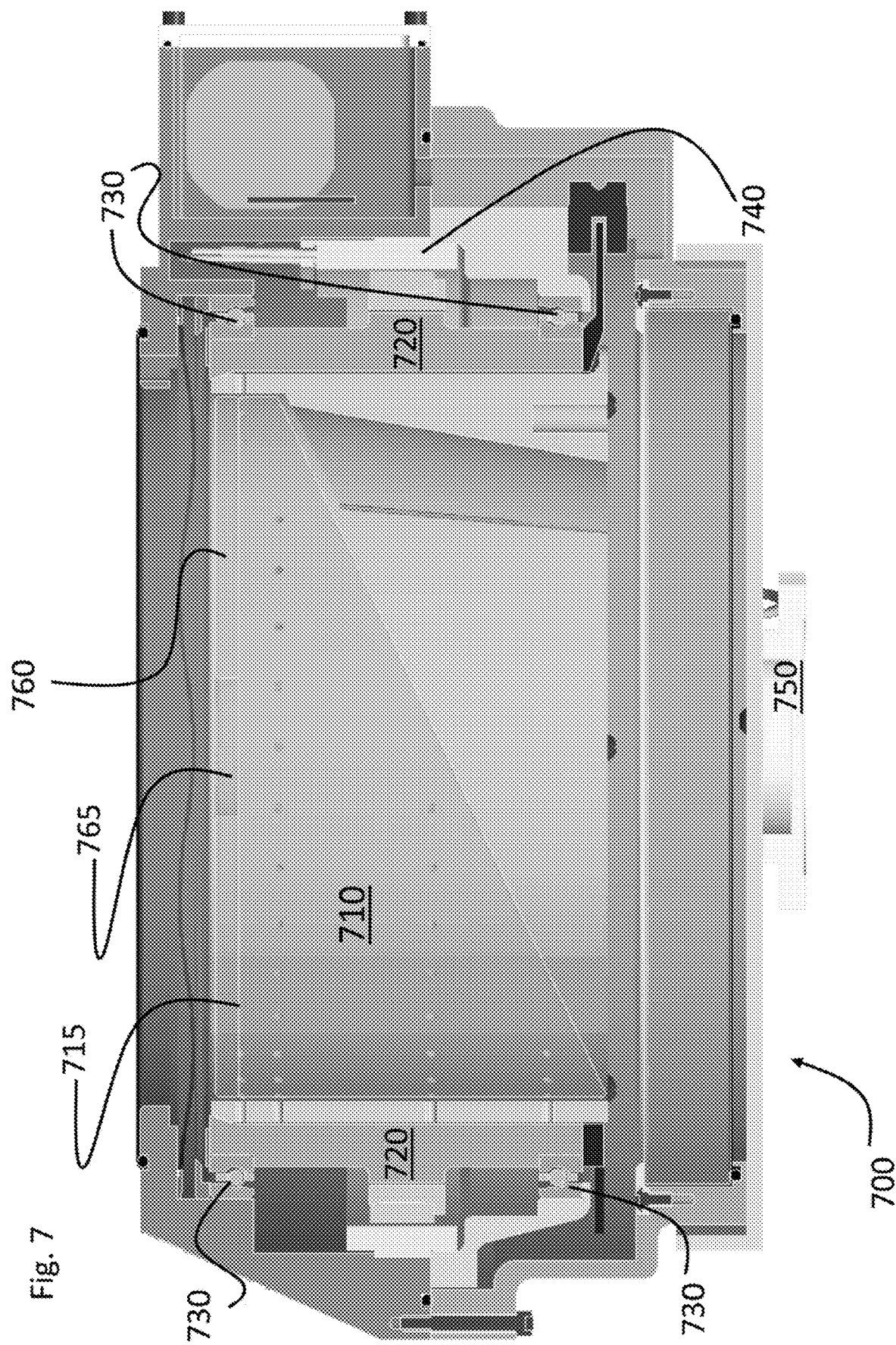

METHODS AND APPARATUS FOR ADAPTIVE MULTISENSOR ANALISIS AND AGGREGATION

CROSS REFERENCE TO RELATED APPLICATIONS

The current application is a Continuation in Part of and claim benefits from the copending U.S. patent application Ser. No. 13/944,082, entitled "METHODS AND APPARATUS FOR ADAPTIVE MULTISENSOR ANALISIS AND AGGREGATION", filed with the U.S. Patent and Trademark Office on Jul. 17, 2013, and which is incorporated herein by reference. Consequently, the current Continuation in Part application is also based upon and claims benefits of U.S. Provisional Patent Application Ser. No. 61/683,304, entitled "METHODS AND APPARATUS FOR ADAPTIVE MULTISENSOR ANALISIS AND AGGREGATION" and filed with the U.S. Patent and Trademark Office on Feb. 15, 2011, and co-owned U.S. patent application Ser. No. 13/027,458 entitled "SELF-ORGANIZING SEQUENTIAL MEMORY PATTERN MACHINE AND REINFORCEMENT LEARNING METHOD" filed with the U.S. Patent and Trademark Office on Feb. 15, 2011, all of which are also incorporated herein by reference.

FIELD OF THE INVENTION

The invention relates generally to methods and instruments for flexible adaptive multisensor data acquisitions and analysis of acquired information in order to generate results applicable to management of resources. In particular, the current invention pertains to a self consistent method for adaptive implementation of overflying multi sensor measurements and derivation of actionable conclusions pertinent to determination of status and proactive management models of at least one distributed resource associated to a geographic area.

BACKGROUND OF THE INVENTION

The instant invention pertains to methods which incorporate flexible data generation and retrieval, integrated data processing, analysis of extensive geographically-distinguishable databases and datasets, and advanced economic modeling and reporting, with nearly-real time financial management and/or financial services arranged to enable intelligent conduct of economic and social policies at scales ranging from single economic or political entities to global institutions and organizations.

The current invention enables development of flexible undatable knowledge management strategies and resulting actions that may be expended in space, time, or social importance to co-evolve with economic and social needs and dynamically respond to gradual or abrupt events and developments. In addition, benefits resulting from various embodiments of the current innovation may be utilized internally to address needs of groups and organizations actively involved and directly performing the methods and steps of the current invention or be marketed and delivered as a knowledge-based service to external clients or customers.

SUMMARY OF THE INVENTION

The present invention pertains to a system for generation and adaptive implementation of overflying multi sensor measurements and derivation of actionable aggregants pertinent to determination of status and proactive management models of at least one distributed resource.

The system includes a set of calibrated overflying multi-sensor detectors arranged for detecting signals from electromagnetic radiation redirected by a plurality of underlying structures having a combination of features having variable scale lengths, a data processing computing device arranged for determination of a set of overflight parameters and arranging and preprogramming the set of overflying multi-sensor detectors for detecting and processing signals from electromagnetic radiation redirected by the plurality of underlying structures having a combination of features having the scale lengths of interest, and an overflying apparatus arranged for enabling overflights and performing in-flight acquisition, preprocessing, and storing of data sets resulting from the multisensor measurements using the set of overflying multisensor detectors.

The system also incorporate a subsystem arranged for transferring the preprocessor data sets to an data analysis computing device arranged for analyzing the transferred data sets using the determined set of overflight parameters and a set of predetermined overflying multisensor detectors calibration data, wherein the data analysis computing device have been arranged for determination of sufficiency of analyzed data, sets for derivation of actionable aggregants pertinent to determination of status and proactive management of at least one distributed resource of interest, and, in a case of insufficient analyzed data sets, determination of needs for additional data sets; a subsystem for harmonization the sufficient analyzed data sets corresponding to the underlying structures, the features, the scale lengths and the actionable aggregants of interest; and determination of satisfactory consistency of the harmonized data sets; and, in a case of unsatisfactory consistency of harmonized data sets, determination of needs for additional data sets; a subsystem arranged for adding the consistent analyzed data sets into a database organized for storage and relational retrieval of data at least regarding the actionable aggregants, underlying structures, the features having the scale lengths of interest, and time, and a subsystem arranged for obtaining external data pertinent to the at least the actionable aggregants, underlying structures, the features having the scale lengths of interest, and time and adding it relationally into the database.

BRIEF DESCRIPTION OF THE DRAWINGS

FIG. 2A-2B are illustrations of a different exemplary embodiment of the present invention.

FIG. 3A-3B are illustrations of another different exemplary embodiment of the present invention.

FIG. 5A-5B are illustrations of yet another different exemplary embodiment of the present invention.

FIG. 7 illustrates schematically another different exemplary embodiment of the present invention.

DETAILED DESCRIPTION

In the following description of embodiments of the present invention, numerous specific exemplary details are set forth in order to provide a more thorough understanding of the present invention. However, it will be apparent to one skilled in the art that the present invention may be practiced without one or more of these exemplary details. In other instances, well-known features of prior art have not been described in detail to avoid unnecessarily complicating the description.

Figure 1:
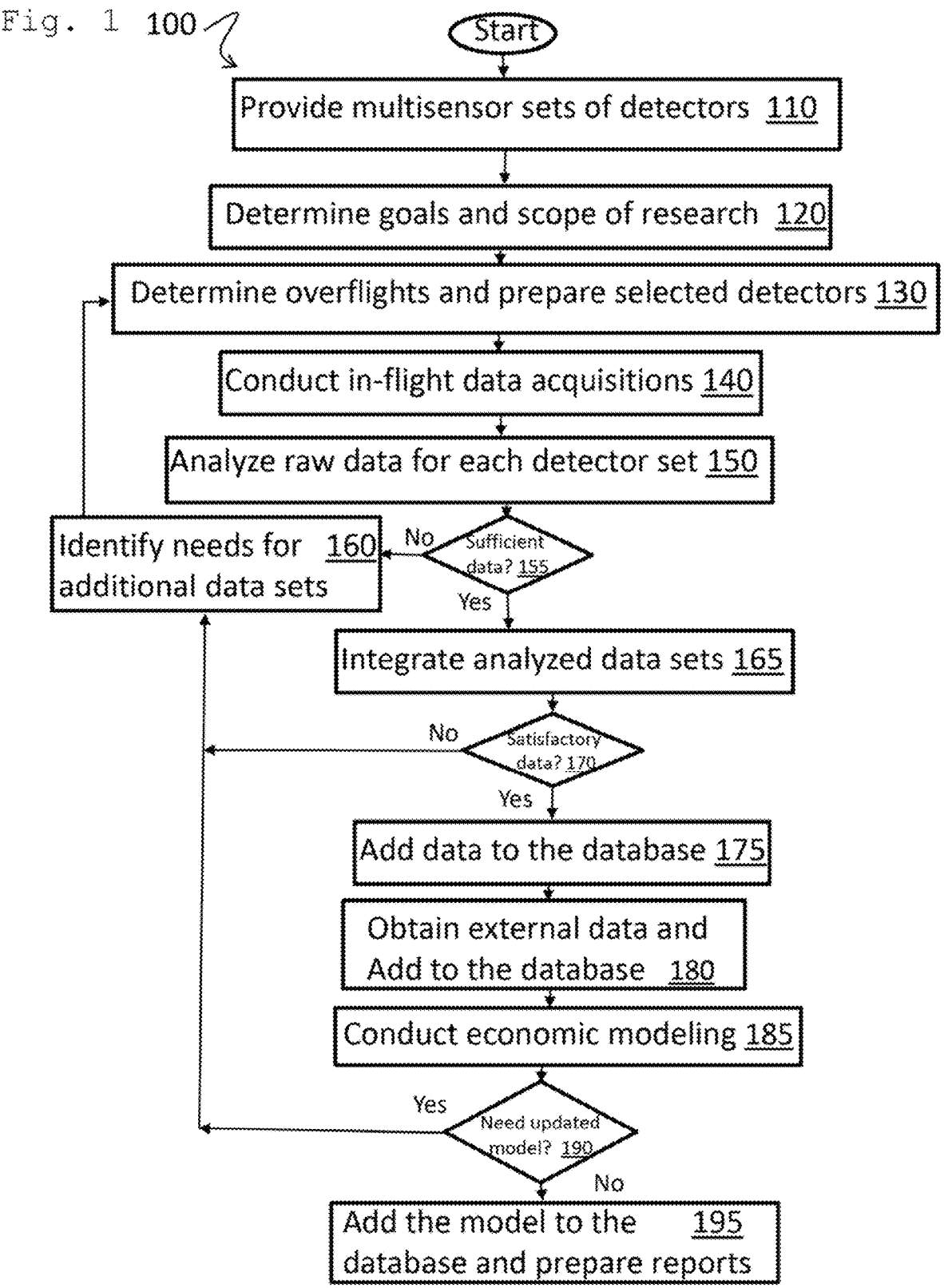
FIG. 1 is a schematic illustration of an exemplary embodiment of the present invention.

One particular self consistent method for adaptive implementation of overflying multi sensor measurements and derivation of conclusions and determinations aggregants pertinent to a group of embodiments of the present invention is illustrated schematically in the FIG. 1 flowchart 100. It includes the step 110 of providing at least one set of calibrated overflying multisensor detectors arranged for detecting signals from electromagnetic radiation redirected by a plurality of underlying structures having a combination of features having variable scale lengths. The set of multisensor detectors may be embodiment-specific and may include sensors and detectors arranged for installation on satellites, airplanes, helicopters, gliders, rockets, unmanned aerial vehicles, ballistic projectiles, aerostats (including kites, free and moored balloons, rigid and flexible airships), and variety of possible combinations (such are, but not limited to, kite/balloons known as "Helikites", motorized or rocket powered gliders known as "rocket-plans", free-dropping payloads, free-dropping or towed parachutes, par-gliders, motorized kites, light and micro-light kites/planes and similar).

Also, the multisensor detectors may be, according to the particular embodiment, purposely arranged and specialized for tusks of interest or multifunctional devices frequently provided by public or private institutions and available as public service or for use on commercial basis. It may be understood that the choice 110 of the set of detectors may be conceptual or flexible and may incorporate several options that may be implemented sequentially, in combination, and/or as alternatives, potentially changing in time and evolving in accordance with changes of goals or needs.

Furthermore, it may be noted that the set of overflying multisensor detectors may be arranged to function in support of, or being supported by additional stationary or surface-transportable detectors arranged to provide additional complementary, supporting, calibration, and/or verification measurements and resulting datasets. Even further, the relevant data may be obtained from historical record, databases, scientific and statistical models and modeled results, numerical simulations and similar.

It may be noted that a step of the choice of sets of overflying multisensor detectors may depend on particular embodiments. For one group of embodiments of the current invention the set of overflying multisensor detectors may be chosen from a group of detectors including visible, IR and UV spectrometers and spectro-photometers; visible, IR, and microwave radiometers, bolometers and spectrum analyzers, RADARs and Doppler RADARs; 2D and 3D LIDARs; and combinations of listed detectors.

In different groups of embodiments of the current invention pertinent to investigations of agricultural and food production resources the aggregants may be chosen from the set of aggregants incorporating soil type, soil curvature, soil-color class, soil texture, soil moisture, soil moisture index, seeding rate and seeding density, germination rate and density, difference vegetation index, normalize difference vegetation index, chlorophyll absorbance and reflectance, chlorophyll concentration and chlorosis factors, photosynthetic rate, observed and expected yields and yield density, covered or exposed surfaces albedo and spectral reflectance, plant or animal numbers and number density, and mixtures and combinations of the listed actionable aggregants.

Therefore, it may be noted that the particular determination of overflight parameters and choices of the sets of overflying multisensor detectors 130 may relate to goals and particular scopes of searches predetermined by potential parties of interest as motivated by particular needs and motivations to conduct particular investigations, modeling and management activities. Accordingly, at least initial determination of scopes and goals 120 of the inquiry to be conducted in the data acquisition stages of the methods in accordance with the current invention may be significant factor determining the overall success rate of the pertinent activities.

The overflight parameters pertinent to the application using space-bourn detector sets may include, but are not limited to, types of geocentric satellite orbit, altitude of geocentric orbit, eccentricity of elliptic geocentric orbit, synchronicity of geocentric orbit, inclination of geocentric orbit. In embodiments utilizing atmospheric areal flights the overflight parameters may include, for example, boundaries of atmospheric areal flight, time limits of atmospheric areal flight, operating altitude of atmospheric areal flight, ground velocity of atmospheric areal flight, and air velocity of atmospheric areal flight.

It may be noted that different embodiments may benefit from results derived from combinations of exo-atmospheric and areal detectors measurements. I may be likely that practitioners of methods according the o of current invention determining overflight parameters for such embodiments may use inherent relative flexibility of areal flight procedures to compensate for relative inflexibility of space-bourn instruments regarding spatial resolution, overflight timing, and/or scanning patterns. For example, the atmospheric areal overflights may be optimize to augment pertinent datasets available from satellite data basis, acquiring particular critical datasets revealing fine features regarded to be beyond the sensitivity limits of space-bourn detectors.

Regarding the step of conducting in-flight data acquisitions 140, one may deduce from above, that it may include segments of obtaining data acquired on extended or regular basis, for example using overflying satellites, and segments of purposely designed data acquisition targeting time and/or position specific information available, for example, only as a result of carefully designed and conducted searches. Consequently, a particular feature of the data acquisition in accordance with the methods of current invention may be related to flexibilities of the data acquisition scheme to react in nearly real time to the aggregate of preexisting information and in-streaming newly acquired results in order to augment and optimize resulting information versus predetermined or newly-evolved goals and scopes of the particular investigation.

Having in mind relative complexity and adaptability of devices and methods of various embodiments of current invention, it may be noted that different data analysis strategies and protocols for processing and analyzing 150 of raw data for all detectors may be utilized. In general, a preference for extensive in-situ data processing may be justified at least because of advantages related to optimization of speed, efficiency, reliability, and security of data transfers. Thus, in many embodiments, at least one data processing and data analysis computing device may be positioned in proximity of the sets of overflying multisensor detectors and arranged to process raw data sets transferred from overflying multisensor detectors, predetermined set of overflight parameters, and at least one set of predetermined overflying multisensor detectors calibration data.

In particular embodiments the acquired data may be communicated to remote processing computational devices for storage and further analysis. Also, one may expect that particular sets of embodiments may utilize appropriate combination of in-situ and remote data, processing including a communication protocol enabling exchange of information such that improvements of data acquisition 140 and/or data analysis 150 may be effected in nearly real time.

It may be also noted that evaluation of sufficiency of processed and analyzed data, denoted by the decision block 155 in FIG. 1, may be performed in parallel or sequentially regarding the actions of the step 150. Again, recognizing potential complexities of the current method, it may be of interest to recognize potential insufficiencies in acquired datasets even during data acquisition step 140 such that corrective and/or remedial actions may be considered, planed and implemented even during contemporary overflights.

It may be also noted that more comprehensive versions of evaluation of processed data sufficiency may be performed subsequent to the active data acquisition 140 and raw data analysis 150 steps of various embodiments of the current method. One of significant results of the evaluation of the decision block 155 may be determination of quality of acquired information win emphasis on detected, probable, and/or apparent insufficiencies in the quality or structure of collected information such that needs for additional data sets may be identified (step 160). Timelines of such determination may be of particular interest considering the iterative features of the current method and potential advantages based on flexibility and adaptability of aforementioned and following steps and operations.

As a related note, a skilled practitioner may realize that the decision block 155 (as well as all subsequent decision blocks of the FIG. 1.) may not be strictly exclusive as customary in algorithms based exclusively on binary logic. Namely, it may be likely in some embodiments that particular segments of information as processed in the step 150 may be simultaneously or sequentially be directed both in the "No" direction to be used in step 160 and in the "Yes" direction to be timely analyzed and integrated in the step 165 (to the extent enabled by the inherent values and qualities of particular information segments).

Step 165 includes activities and processes of harmonizing the sufficient analyzed data sets resulting from the step 150. The integration may correspond to the underlying structures, the features, the scale lengths and the actionable aggregants of interest. Also, it may incorporate information regarding determined satisfactory consistency of the harmonized data sets, and, in a case of unsatisfactory consistency of harmonized data sets, needs for additional data sets as per step 160. It may be noted that an iterative repetition of aforementioned steps 130-160 may be performed until the sufficiency of the available data sets may be established, as schematically illustrated in FIG. 1 by the "Yes" direction of the decision block 155.

The step of evaluations corresponding to the decision block 170 may include further processing of the available data pertinent to evaluation of usefulness of the newly-generated data sets (for example, pertinent to the particular aggregants or groups of related aggregants) relative to the known features or previously determined information. Findings of significant discrepancies or contradictions, for example between different segments of newly-generated data sets or relative to the pre-existent data or previously-established findings and/or conclusions may result in an unsatisfactory determination ("No" of the decision block 170) which may require additional investigations yielding additional data sets as these aforementioned in discussions of the step 160. As evident from the flowchart 100, an expended iterative process including the steps 130-170 may be performed until the aforementioned difficulties may be overcame and satisfactory data obtained.

The step 175 pertains to actions of appropriate organization, storage, and preservation of the datasets emerging from the evaluations under the decision block 170 into at least one database structure. This step includes adding the consistent analyzed data sets into a database organized for storage and relational retrieval of data at least regarding the actionable aggregants, underlying structures, the features having the scale lengths of interest, and time. In addition, the step 175 may include actions directed toward planning, establishment, configuration, maintenance, upgrades, and management of software and hardware used for function and development of the at least one database, as well as several processes and activities directed toward communication and data exchange with other data-storage and processes activities of pertinent to other (e.g. external) publicly accessible or restricted-aces data processing establishments.

Subsequent step 180 concerns obtaining external data pertinent to the at least the actionable aggregants, underlying structures, the features having the scale lengths of interest, and time, and adding it relationally info the appropriate database or databases. This may include a broad variety of related data domains including, but not limited to, historic and time accumulated information, geological and/or climate records, economic and market statistics, demographic and public policy information, and/or integrated and multi-disciplinary information and data combinations.

The step 185 pertains to processes and actions directed toward construction of at least one economic model utilizing the at least one actionable aggregant pertinent to determination of status and proactive management models of at least one distributed resource. It may be noted that scale, scope, complexity, goals, initial assumptions, and/or underplaying economic theories of the economic modeling 185 may strongly depend upon embodiment specific conditions, circumstances and limitations.

As an example, embodiments utilizing economic modeling based on "Hybrid-Maze" Simulation Model for Corn Growth and Yield commercially available from University of Nebraska, Lincoln, may require as input info: geolocation (position, size, elevation etc.) of the area of corn cultivation, particular time information (years, seasons, dates of interest for corn cultivation, historic wetter information, hydrological data pertinent to surface and underground wither deposits, meteorological records pertinent to atmospheric conditions (clouds, winds, aerosols, fugue, frosts . . . ), information related to pedology (including general soil typology, soil morphology, pedogenesis, edaphological features (including aspects pertinent to agrology, agrophysics, and "environmetology"—environmental soil science,) of the locality of interest. It may be of particular interest to provide accurate and up-to-date information on soil mobster content (e.g. in the form of soil moister index obtainable, for example, from satellite or airborne radiometric measurements such are "SMOS" and "HYDROS" Satellites from NASA, or Passive and Active L- and S-band Radiometer (PALS) instruments flown on NSF's Lockheed (now Lockheed Martin) C-130 aircrafts).

The step of evaluation of needs for updating of available economic models, schematically indicated by the decision box 190 of FIG. 1, may include scheduled evaluations based on regularized schedules of data updates and/or reevaluation, and reevaluations induced by previously unforeseen or unplanned events including natural or men-caused emergences (e.g. floods, fires, storms, volcanic eruptions, economic and socio-political crises and disturbances, market instabilities, and similar conditions). It is a significant feature of the methods in accordance with the current invention that it may react flexibly and appropriately to virtually any change in conditions or demands all the way to those which may fundamentally alter the goals and scopes of the particular investigation. Furthermore, the above changes and flexibilities may be implemented such that substantially all valid preexisting data, information, processes, codes, databases, and concepts may be reused in existing or adapted forms for an efficient generation of new or updated concepts and pertinent supporting data. Therefore, embodiments of current invention may be responsible for up-to-date information enabling forecasting, risk analysis, planning, and/or near real time reaction in cases characterized by evolving, escalating, or crisis conditions.

In some applications of the current invention the updated economic models and pertinent information may be stored into relational databases and/or utilized for preparation of appropriate reports as in step 195 of the FIG. 1. It may be noted that the scope and contents of the report may strongly depend upon particular circumstances pertinent upon the inquiry of interest. It may be also noted that aforementioned features of timeliness and flexibility of the information generation process may be reflected in the reports of interest. As one example, the information generated by the methods of current invention may be used as an introductory, supplementary, or preliminary supplement for any monthly or periodic World Agricultural Supply and Demand Estimates (WASDE) Reports as available from U.S. Department of Agriculture Economics, Statistics and Market Information System (ESMIS) as available, for example, from http://usda.mannlib.cornell.edu/MannUsda/homepage.do, as at Apr. 26, 2016.

The systems discussed above have been designed to provide high efficiency, high resolution 3D LIDAR imaging. Use of single photon sensitive microchannel plate photomultipliers, combined with our in-house low-dead-time timing receivers, allows for operations in high solar noise environments and to penetrate obscurants such as thin clouds, ground fog, battlefield dust, and tree canopies. The 532 nm wavelength may take advantage of sensitive, low noise, fast recovery array detectors and efficient spectral filters available only in the visible wavelength regime. The segmented anode photomultipliers, combined with dual wedge optical scanners, allow for coverage of large FOVs with high spatial resolution and measurement rates measured in Megapixels per second. The highly flexible scanners can be used to generate contiguous 3D images on a single overflight from high velocity aircraft (with linear raster or conical scans) or from a quasi-stationary platform in 3D camera mode (using rotating line or spiral scans).

An example of an embodiment incorporating space-bourn data acquisition is illustrated in FIGS. 2A-2B. The images in FIGS. 2A-2B represent gridded Normalized Difference Vegetation Index (NDVI) data used customarily in remote sensing application as a representative (reciprocal) measure of photosynthetic activities associated with surface areas of interest. The illustrated NDVI in FIGS. 2A-2B (given as a grading in false gray color such that darker hues represent decreasing values of NDVI=(KIR−VIS)/(NIR+VIS), normalized reflectance in Near Infra Read (NIR) and Visible (VIS) in appropriate segments of measured reflectance spectrum.

The data in FIGS. 2A-2B have been generated as 16 day composites of measurements from the MODIS instrument of the Aqua satellite with 250 m resolution (MODIS VI, product from the MOD13Q1 database available for example from NASA) over the common 1200 km×1200 km area of Eastern U.S. The illustrated datasets indicate NDVI mostly during April (A) and July (B) of 2011, and include a point of interest 200 in Eastern Maryland proximal to the 38°43'50" N Latitude and 76°41'02" W Longitude.

It may be noted without a detailed analysis that FIGS. 2A-2B indicate generally self-similar feature that arboreal, grazing/movable, and/or cultivated lands differ significantly in the NDVI related aggregants from urbanized or "developed" lands or water surfaces, but the selected scale lengths and resolutions may be relatively insensitive to ("normal") seasonal or vegetative cycles related changes especially over the areas exhibiting diversities characteristic of Eastern/Mid-Atlantic region of the United States. In particular, very limited information may be available on the particular locality of interest proximal to the 38°43'50" N Latitude and 76°41'02" W longitude, predominantly because of the choice of the MODIS instrument and it's spatial and temporal resolutions.

Figure 3A:
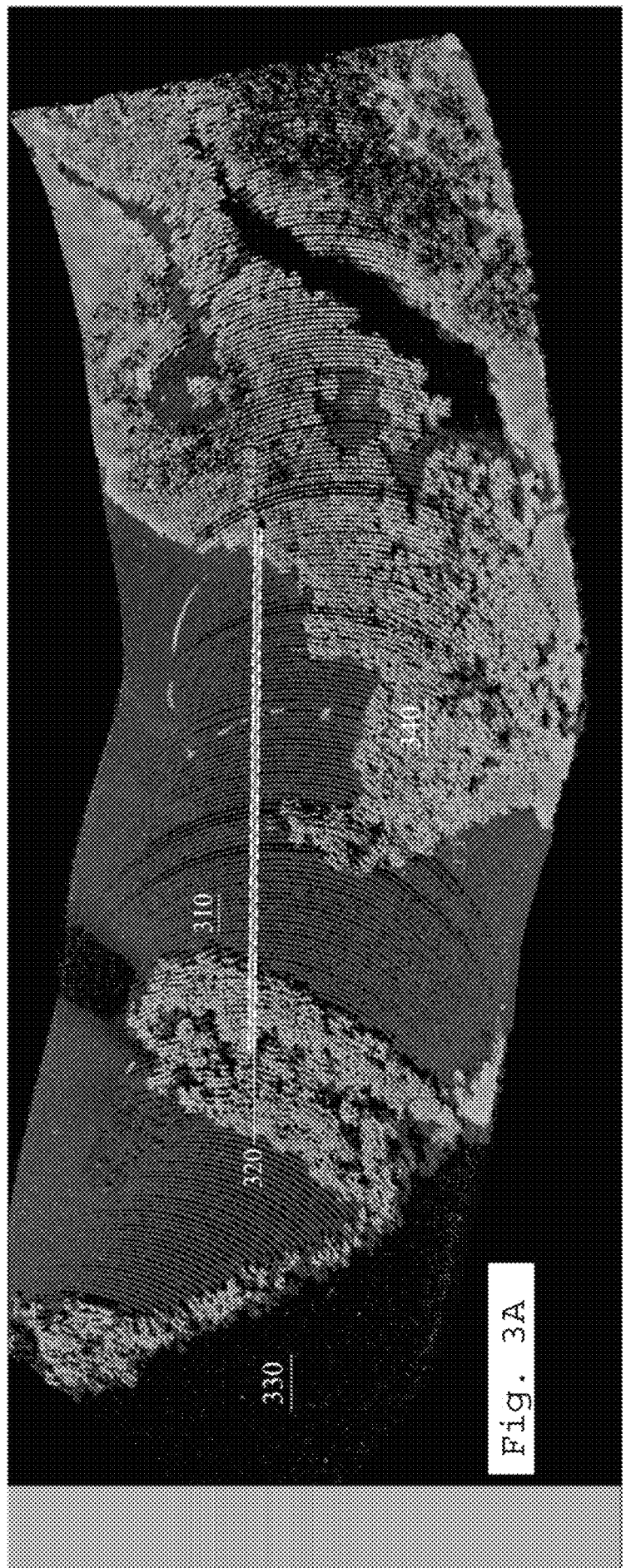

Other embodiments my relate to more detailed rendering of features associated to the proximity of the point of interest at 38°43'50" N Latitude and 76°41'02" W Longitude. One example utilizing data collected by the aforementioned University of Texas "Icemapper" operated in 3D LIDAR conical scan camera mode is illustrated in FIG. 3A-3B. FIG. 3A illustrates a portion of aggregated data generated during a Beechcraft King Air 90C airplane 700 m overflight on Oct. 23, 2011. The illustrated features may be more convenient to interpret from the information in FIG. 3B having the scan area 350 of the FIG. 3A superimposed on an aerial photo as available (Jun. 28, 2012) from the "Google earth" web application of Google Inc. registered at 1600 Amphitheatre Parkway Mountain View, Calif. 94043. In addition, in FIG. 3B one may note position markers 360 indicative of the surface projections of the position of the Beechcraft King Air 90C airplane at the particular time of proximal 3D LIDAR data acquisition.

The 3D LIDAR scene in FIG. 3A includes a corn field 310 separated from the Patuxent River 330 by arboreal areas 340. It may be noted that FIG. 3A also include an indicator 320 marking the data portion used for generation of vertical profiles illustrated in FIG. 4A-4C. Three vertical profiles a-c have been recorded during three distinct phases of corn vegetative cycle, of which FIG. 4A may be correlated to germination and seedling early development phase (spring of 2011), FIG. 4B may be correlated to full grown cob bearing phase of mature corn (Jul. 15, 2011), while FIG. 4C relates to the corn field 310 after the corn has been harvested (Oct. 23, 2011).

Figure 4A:
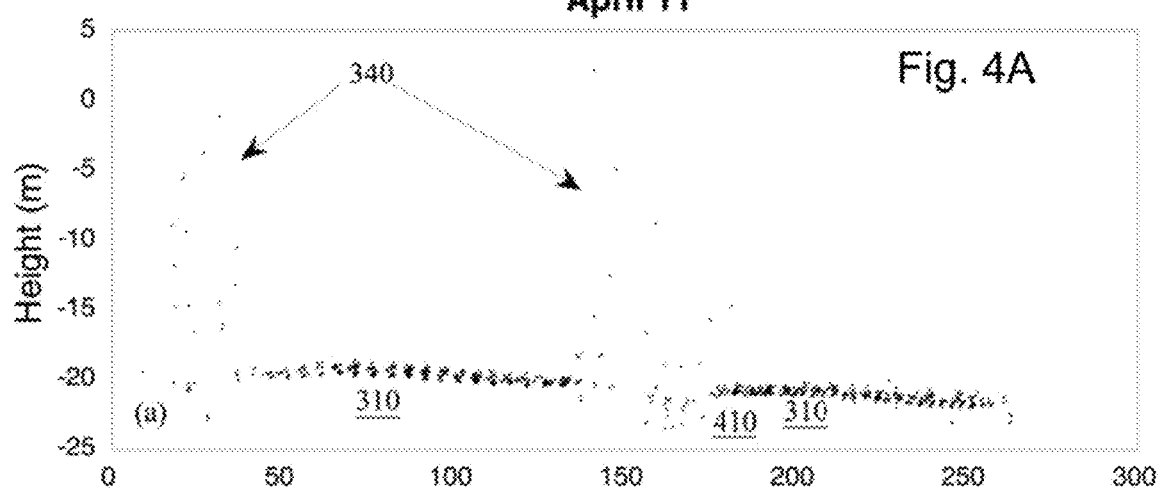
FIG. 4A-4C are illustrations of yet another different exemplary embodiment of the present invention.
Figure 4B:
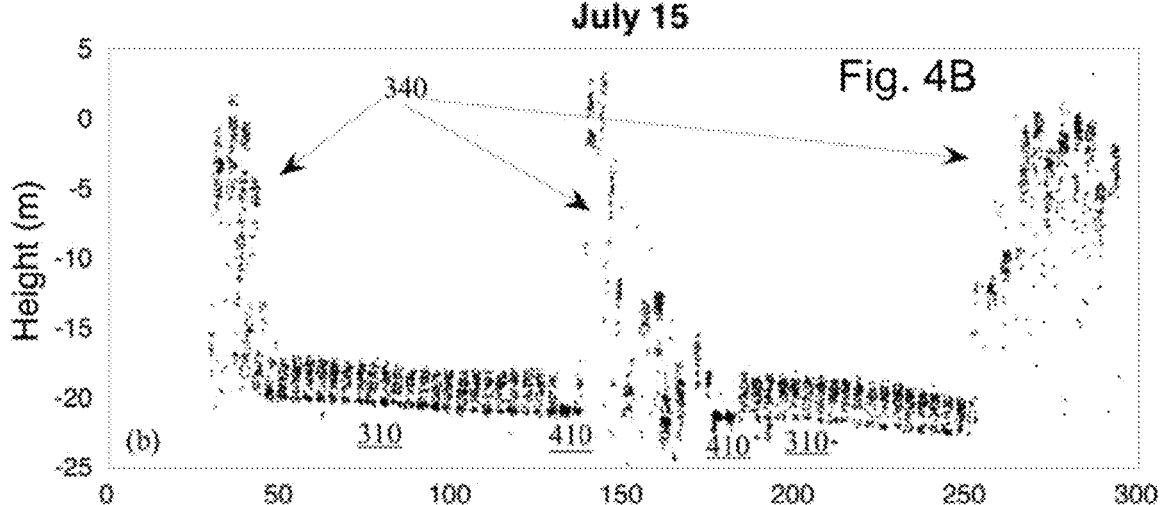
Figure 4C:
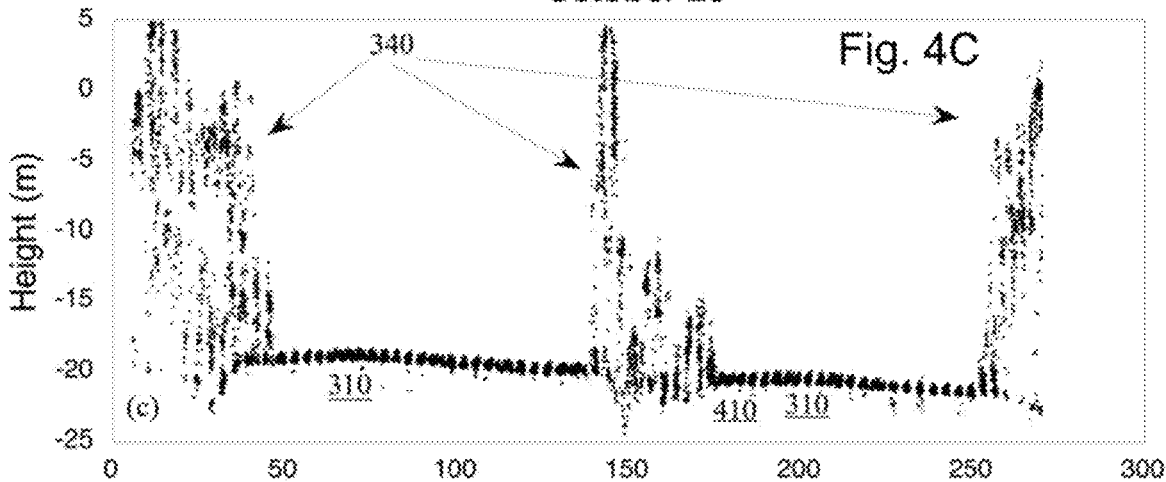

It may be of interest to note that FIG. 4A, pertinent to corn germination and seedling sprouting and early development phase (spring of 2011) may be used as a basis for determination of ground level and its gradients mostly conditioned by the presence of the Patuxent River 330. It may be noted that the profiles in FIG. 4A-4C have been inverted with respect to the indicator 320 of FIG. 3A. Namely, the profiles in FIG. 4A-4C are plotted such that the abscissa is pointing generally into westerly direction (toward the closest bank of the Patuxent River 330) such that ground level of the corn field 310 rises in the opposite direction. For that purpose, the data points associated with the arboreal areas 340 at larger x values ("the right side" of the profile in FIG. 4A) have been filtered out and not included in the FIG. 4A, but distinguishable in FIGS. 4B-4C.

In addition, one can note significant corm field 310 related features including one of access roads surface 410 associated with the edges of the field 310. Also, a detailed statistical analysis of the data, particularly in FIG. 4B may be used for yield estimates (both corn cub and corn total biomass related) up to estimates of harvest losses and residues (for example in FIG. 4C).

In different embodiments, detailed investigation of water surfaces may be conducted using 3D LIDAR imaging techniques. In an exemplary embodiment illustrated in FIGS. 5A (surface projection) and 5B (vertical cross-section) of waters and embankment of aforementioned Patuxent River 330 proximal to the position of interest 38°43'50" N Latitude and 76°41'02" W Longitude have been illustrated. One may note that a systematic survey of this particular kind may yield data pertinent to surface and underground water flow, pollution, erosion, soil moister index, and other aggregants.

Furthermore, in embodiments utilizing combination of different aforementioned detectors and detector combinations, an issue of combining results from different detector measurements may be of importance. In such embodiments, information generated by multiple detectors measuring common areas of interest may be imputed into a hierarchical network such is the network 20 of FIG. 1 of the incorporated copending U.S. patent application Ser. No. 13/027,458, for pattern analysis and subsequent processing. In similar embodiments, the different detectors outputs may be inputted in individual networks 20 forming a network of networks as illustrated in FIG. 6 of the above incorporated Patent Application.

In yet another set of embodiments, 3D LIDAR imaging have been applied at an exemplary scene in Easton Md. (at Commerce Drive, Easton, Md. 21601) using a HERQLS 3D LIDAR, instrument from altitudes of 7500 ft. and 9000 ft. Two corresponding scenes 600 and 601 obtained during two separate flights, the scene recorded from the altitude of 7500 ft. have been illustrated in FIG. 6A, while the scene recorded from the 9000 ft. have been illustrated in FIG. 6B. during two different flights. The flights utilized different flight plans and overflight patterns are flown under similar external conditions. The HRQLS 3D LIDAR have been operated using a single wedge scanner arranged for a conical scan pattern with scan deflection angle of approximately 9.7° scan deflection angle and 20 Hz scan frequency.

Figure 6A:
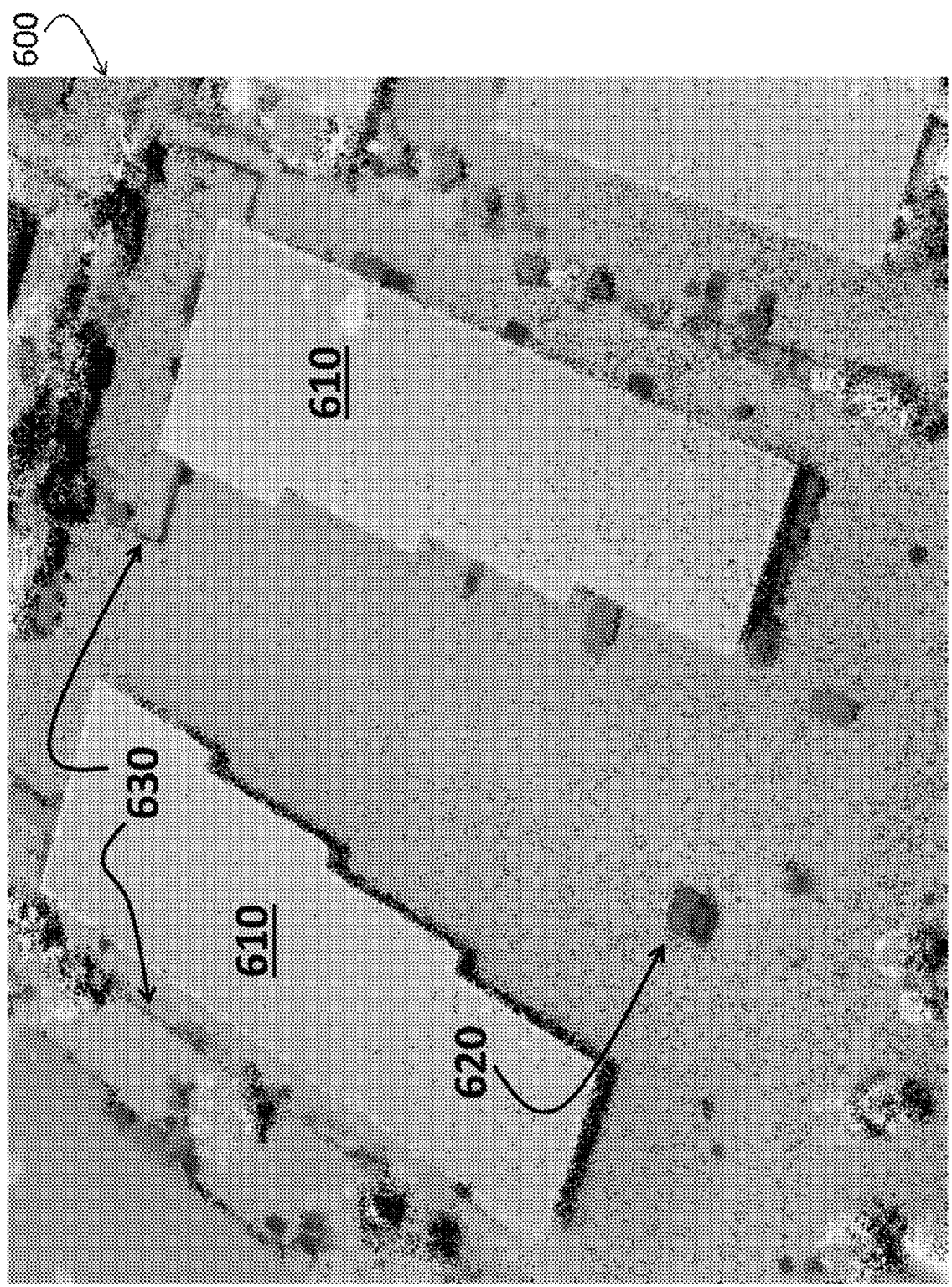
FIG. 6A-6B are illustrations of yet another different embodiment of the present invention.
Figure 6B:
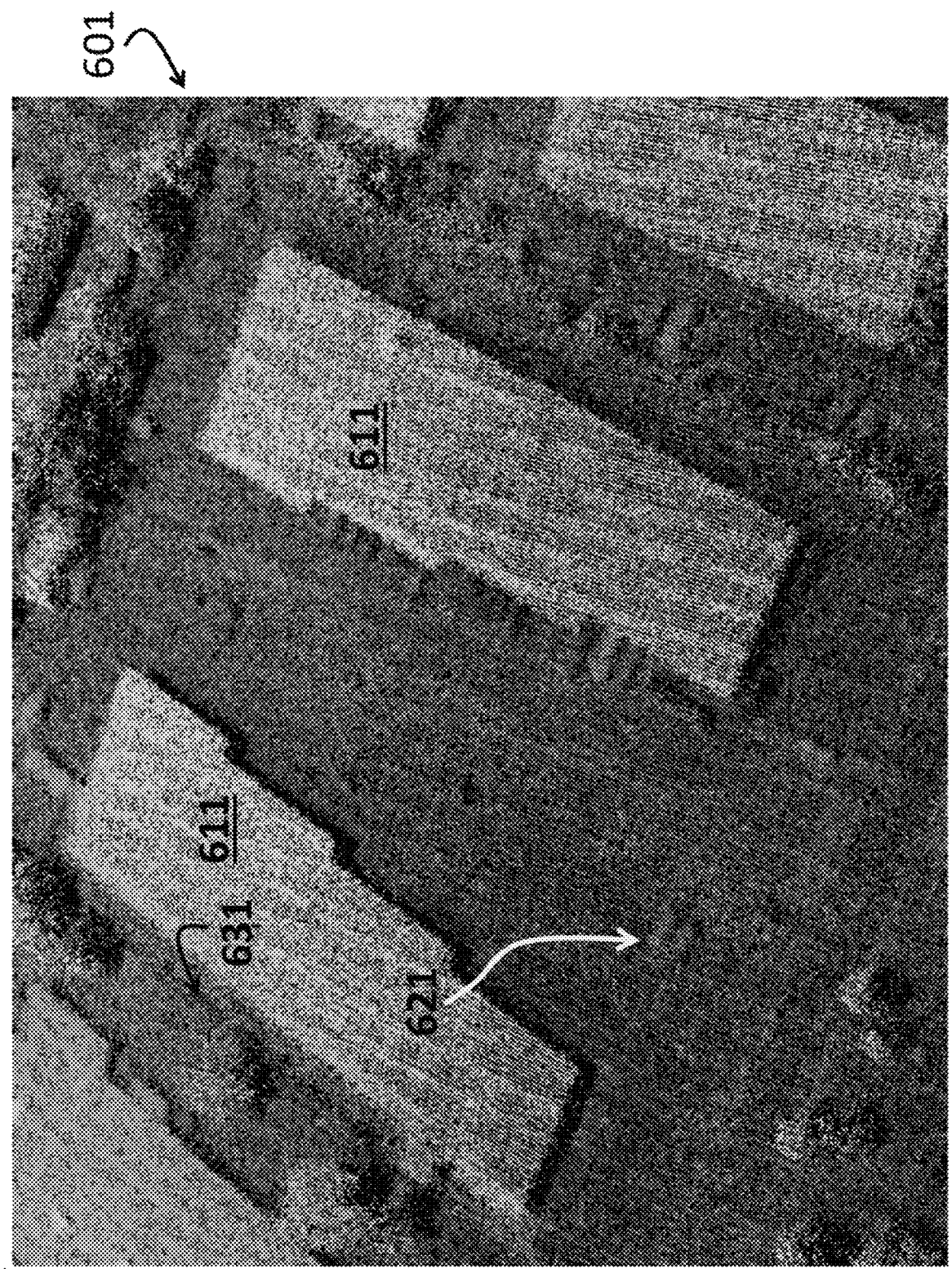

It may be noted that structures in FIG. 6A exhibit significantly higher point cloud density (relative to that in FIG. 6B) resulting in superior definition of boundaries of imaged objects, including commercial structures 610 and 611, and corresponding vehicles 520 and 521. This feature may be also material in identification and detection of objects and structures having reduced reflectivity for example because of significant extend in or along specific surfaces or directions. As an illustrative example, fences 630 are readily identifiable in FIG. 6A, while the corresponding structures 631 in FIG. 6B are close to or below identification thresholds.

A rotating optical wedge has been recognized in prior art as one way to generate a conical scan for terrain mapping LIDARs. Known co-axial system with a single wedge is recognized as relatively compact systems with high pointing stability. However, as the flight altitude increases or at very high scan speeds, the transmitter and receiver become misaligned because of the relative displacements of the wedge caused by the wedge rotation during the round trip time of the light pulse emitted by the LIDAR and subsequently reflected from particular features of the scanned scene. Thus, the receiver optical axis must lag behind the transmitter optical axis. The amount of lag depends on the flight altitude (round trip time) and the scan speed.

One way to address the point ahead issue may be considered analyzing the scanner 700 illustrated in FIG. 7. Here, a scanning optical wedge 710 has been supported by a support structure 720, arranged to be rotated on bearings 730 by an electromotor 740. When not in use the scanner may be protected by a protective cover 750.

A compensator optical wedge 760 (usually having and opening 765, smaller thickness, and smaller wedge angle than the scanning optical wedge 710) may be coupled to the scanning optical wedge 710 (for example, associated with one flat surface 715 of the wedge 710) and arranged to deflect the only the incoming receiver beam of laser light while allowing the transmitter beam to pass through the opening 765 with no deflection (correction) by the compensator wedge 760.

As mentioned above, in many embodiments the compensator optical wedge 760 deflection angle may be smaller relative to such of the scanning optical wedge 710, being arranged to compensate for the customarily smaller look ahead corrections angle required for applications having the altitudes and scan deflection angles comparable to the scans as illustrated in FIGS. 6A-6B.

In the above embodiments, the orientation of the compensator wedge 760 was may be arranged to be close to perpendicular to the scanning optical wedge 710. For the fin compensation, the compensator wedge 760 may be allowed to vary slightly (25% or less) from its $\pi/2$ (90°) relative orientation by an angle $\varphi$ (i.e. $-\pi/8 \leq \varphi \leq \pi/8$). Since the transmitter only sees the optical wedge 710 with a deflection conical scan half angle $\alpha$, the pointing vector to the center of the transmitted spots on the ground may be given as below in a component form in a rectangular right-handed coordinate system associated with the local ground point at t=0 and oriented such that "y" component is equal to 0 at time t=0 while the "z" component is vertical in the opposite direction from the observer at the height "h" (written as a column of scalars in between the "||" signs) and may be represented by $$T(0) = h \begin{Vmatrix} \tan\alpha \\ 0 \\ -1 \end{Vmatrix} \quad (1)$$

while, at the same instant, the receiver is now pointed along the vector $$R(0) = h \begin{Vmatrix} \tan\alpha - \tan\beta\sin\varphi \\ -\tan\beta\cos\varphi \\ -1 \end{Vmatrix} \quad (2)$$

where $\beta$ is the angular deflection of the compensator wedge 760. After the pulse travels to the surface and back (during which the wedges 710 and 760 rotate by an angle $\phi$), the receiver vector is $$R(\phi) = \begin{vmatrix} \cos\phi & -\sin\phi & 0 \\ \sin\phi & \cos\phi & 0 \\ 0 & 0 & 1 \end{vmatrix} R(0) = h \begin{vmatrix} \cos\phi(\tan\alpha - \tan\beta\sin\varphi) + \sin\phi\tan\beta\cos\varphi \\ \sin\phi(\tan\alpha - \tan\beta\sin\varphi) - \cos\phi\tan\beta\cos\varphi \\ -1 \end{vmatrix} \quad (3)$$

For the point ahead compensation to perform properly, the intensity of difference vector between vectors $R(\phi)$ and $T(0)$ should be approximately equal to zero in magnitude, i.e.

$$\Delta RT = R(\phi) - T(0) = h \begin{vmatrix} \cos\phi(\tan\alpha - \tan\beta\sin\varphi) + \sin\phi\tan\beta\cos\varphi - \tan\alpha \\ \sin\phi(\tan\alpha - \tan\beta\sin\varphi) - \cos\phi\tan\beta\cos\varphi \\ -1 \end{vmatrix} \quad (4)$$

should be minimized. From (A) the magnitude of the difference vector is give by $$|\Delta RT|^2 = h^2[2\tan^2\alpha(1-\cos\phi) + \tan^2\beta - 2\tan\alpha\tan\beta(\sin\varphi(1-\cos\phi) + \cos\varphi\sin\phi)] \quad (5)$$

It would be desirable to find the values of $\beta$ and $\varphi$ which minimize the distance between the transmit beam center and the corresponding pixel center. Differentiating (5) with respect to tan setting the result equal to zero yields $$\tan\beta = \tan\alpha[\sin\varphi(1-\cos\phi) + \cos\varphi\sin\phi] \quad (6)$$

Similarly, differentiating (5) with respect to $\varphi$ and setting that result equal to zero yields $$1 - \cos\phi = \sin\phi\tan\varphi \quad (7)$$

which can be reduced to $\tan\varphi = \tan(\phi/2)$. Thus, the optimum clocking angle for the compensation wedge is $$\varphi = \frac{\phi}{2} \quad (9)$$

Substituting (9) into (6) yields the optimized deflection for the compensator wedge 760, i.e.

$$\tan\beta = 2\sin\left(\frac{\phi}{2}\right)\tan\alpha \quad (10)$$

Substituting (9) and (10) into (5) yields the optimized result that there is no displacement between the transmitted beam center and the corresponding receiver pixel center, i.e.

$$|\Delta RT| = 0$$

Figure 8:
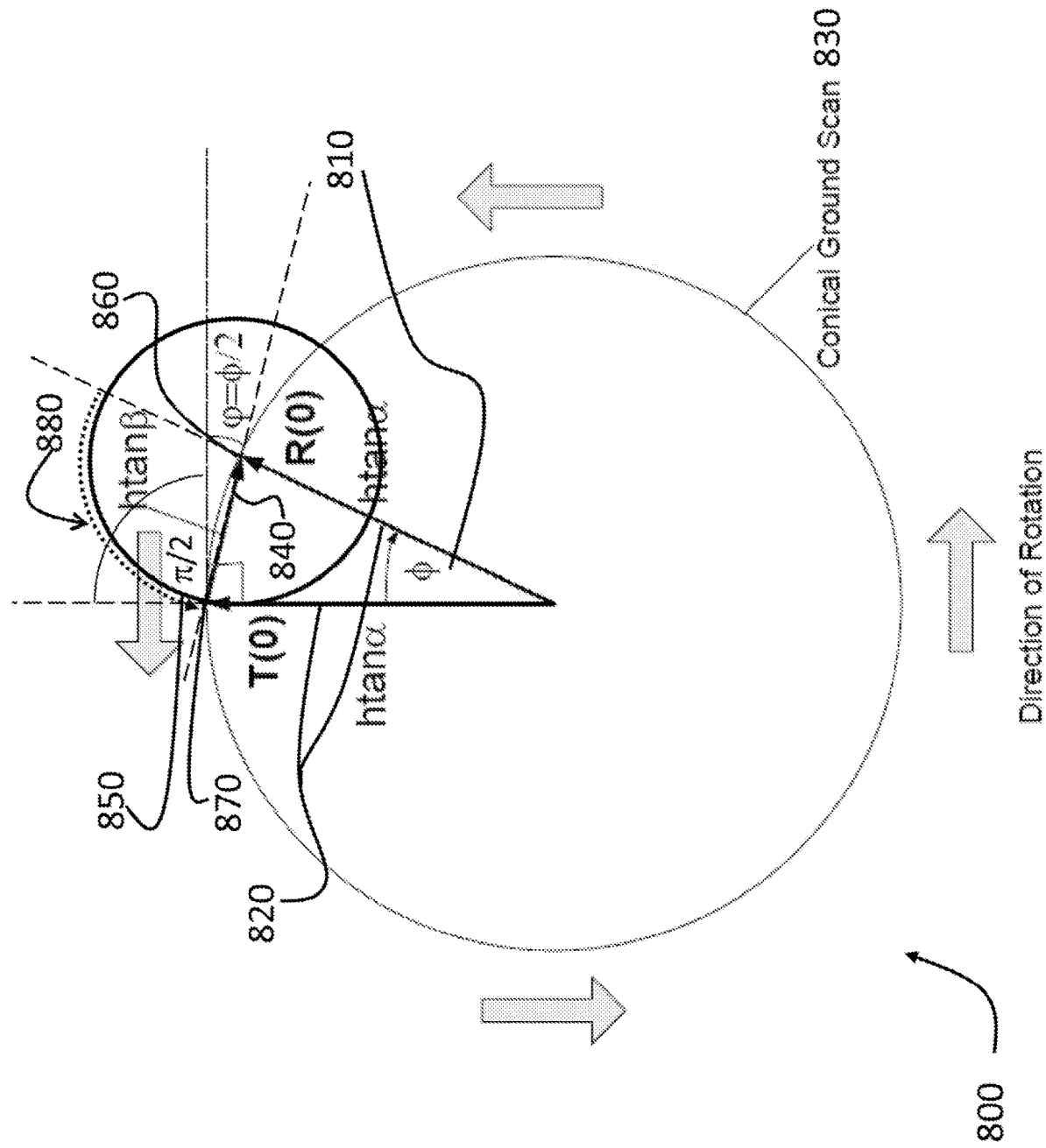
FIG. 8 illustrates schematically additional exemplary embodiment of the present invention.

The above derivation may be illustrated schematically in FIG. 8 which provides a schematic representation 800 of the relationships between pertinent variables and parameters of the above analysis. As indicated above, the angle $\phi$ 810 is the angular displacement by rotation of the scanning optical wedge 710 daring the roundtrip photon pulse time of flight. The h tan $\alpha$ is the radius 820 of the conical ground scan circle 730 (consisting of an array of loci—"pixels" at which the transmitted vector "T" points during the scan) from which the scanning photons may be reflected by objects associated with the ground, where h is the height and the deflection angle $\alpha$ is the conical scan half angle. The h tan $\beta$ is the distance 840 between the transmit and receive FOVs (and, in analogy with the ground scan circle 830, it corresponds to the deflection circle 850 of the reflected photons from the ground pixels at the detector height as deflected only by compensator optical wedge 760), while $\pi/2+\varphi$ is the optimized shift phase angle 880 between the deflection directions of the main scanning optical wedge 710 and the compensator optical wedge 760, where $\beta$ is the angular deflection of the compensator optical wedge 760.

The schematic 800 allows for following graphic interpretation of the look ahead corrections of the above embodiment based on composition of deflection circles 830 and 850. The compensator optical wedge 760, arranged to rotate with the scanning optical wedge 710, performs optimal correction when oriented with respect to the scanning optical wedge 710 by the optimized phase angle shift 880 ($\varphi+\pi/2$) such that corresponding pixel 860 at which the receiving pointing vector "R(0)" points has been deflected back by the compensator optical wedge 760 such to correspond with the pixel 870 at which the pointing vector T has been pointing at the time of transition of the pulse. Therefore, the look ahead corrections may be interpreted as back-deflection along the circle 850 by the compensator optical wedge 760 optimally phased by the additional small phase shift angle $\varphi=\phi/2$, such that pointing of vectors $R(\phi)$ coincides with the pointing of transmitted vector T(0).

It may be noted that the optimized phase shift angle may depend upon the height h, scan frequency, and the properties of the optical arrangements including the wedges 710 and 760. Thus, in some embodiments small errors in shift angle prearrangements, coupled with uncertainties in height, scanning frequency, and pointing control may cause misalignments. Furthermore, having in mind that the above errors may be small in many embodiments, the round trip time of the photons may be also be relatively short (e.g. versus the scanning time) and, consequently, the angles $\phi$ and $\varphi$ may be also significantly smaller than $\pi$, the circles 830 and 850 may intersect substantially perpendicularly (i.e. having nearly perpendicular tangents at the intersect point). There, even relatively small errors in corrections along the circle 850 may result in complete miss of the "pixels" arranged along the ground scan circle 830. Therefore, rather than being erroneously assigned to the neighboring pixels and subsequently recovered, for example by statistical and numerical filtering methods the returns may be irreversibly lost. For such embodiments utilizing point ahead-correction methods and systems having angular deflection circles of the compensating systems intersecting or approaching the ground scan circles more gradually may be of interest.

Figure 9:
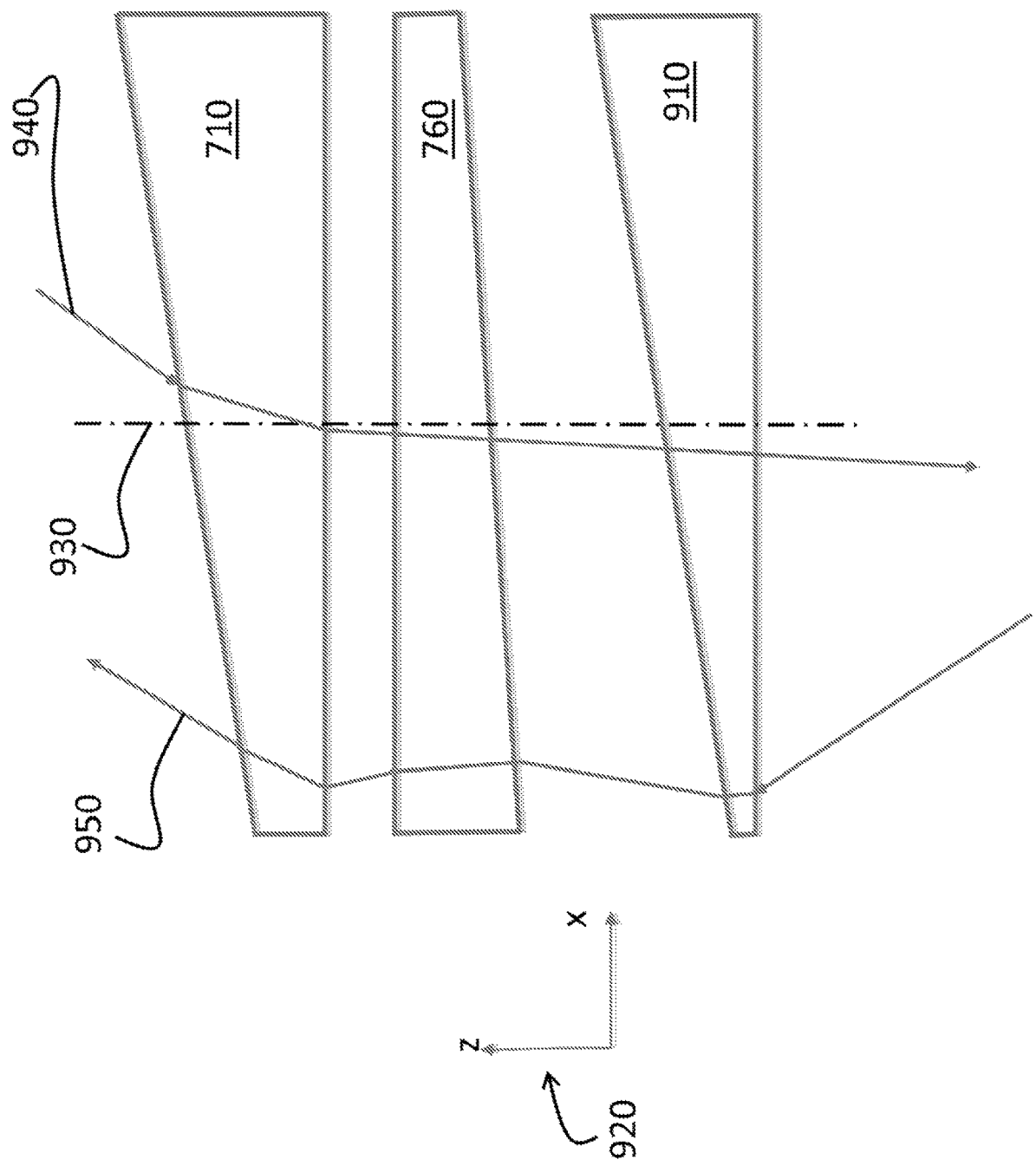
FIG. 9 illustrates schematically another additional exemplary embodiment of the present invention.

One class of such embodiments have been schematically illustrated in FIG. 9. There, an additional optical wedge 910 having an opening that allows the transmitted photons 940 (including individualized photons, batches of photons, and/or light beams) to pass through (similar to the opening 750 of the compensator optical wedge 760), have been shown schematically in FIG. 9 to indicate possible arrangement with regard to the aforementioned coordinate system 920. All the wedges 710, 760, and 910 have been arranged to co-rotate around the axis 930, while the relative phase angles can be adjusted and looked to with respect to the predetermined values.

As in the preceding embodiments, the transmitted photons 940 interact only with the scanning optical wedge 710 while clear the wedges 760 and 910 via the pertinent openings (e.g. the opening 650, while a predominant portion of the received and collected photons 850 have been arranged to be deflected by all wedges 710, 760, and 910. Therefore, as before, one may chose the geometry and optical properties of the wedges 710, 760, and 910 such that radii of the displacement circles are given by h tan $\rho$, h tan $\sigma$, and h tan τ respectively (where, as above, the ρ, σ, and τ represent wedge displacement angles or conical scan half-angles).

It may be also noted by the practitioners that the embodiments having the additional wedge (such as in FIG. 9) offer more flexibility in relative phase angles arrangements. One of such particular arrangements of interest has been schematically illustrated in FIG. 10. In analogy with the embodiments represented in FIG. 8, the conical ground scan circle 830 having ground radius of h tan ρ have been enabled by the deflection of the scanning wedge 710. In this embodiment, as the angle φ 810 is the angular displacement by rotation of the scanning optical wedge 710 during the roundtrip photon pulse time of flight (same as indicated above). Thus, as above, the point ahead compensation (look ahead correction) represents association of the pixel 870 such that corresponding pixel 860 at which the receiving pointing vector R(0) points has been deflected back by the compensator wedge 760 such to correspond with the pixel 870 at which the pointing vector T has been pointing at the time of generation of the pulse, beam, or other set of correlated photons. In the instant embodiment, the correlation may be achieved by deflecting the receiving photons by the wedge 760 phase shifted by with respect to the wedge 810 by a first angle ξ 1010 into an intermediate pixel 1020 and subsequently shifting the intermediate pixel 1020 to correspond to the pixel 870 using the additional wedge 910. As the additional wedge have been arranged with zero phase shift relative to the scanning wedge 710 the shifting out of the pixel 1020 have been achieved approaching 870 co-tangentially (i.e. having substantially zero intercept angle between the tangents on the circles 830 and 1030 at the point 870).

Figure 10:
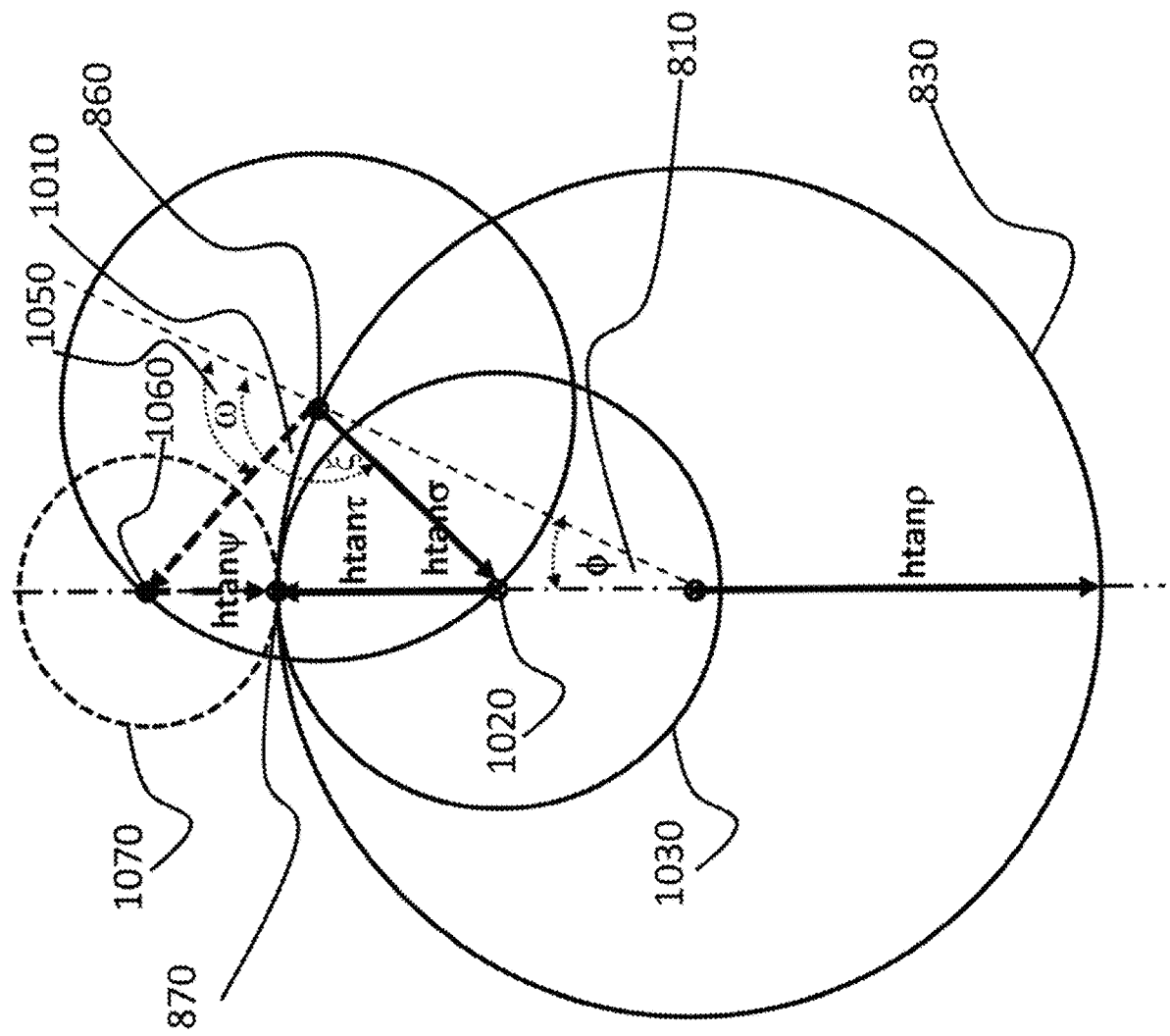
FIG. 10 illustrates schematically yet another exemplary embodiment of the present invention.

It may be noted by direct observation of FIG. 10, that at least another co-tangential solution exists. Namely, for the phase shift angle ω 950 of the wedge 760, the pixel 860 may be shifted into another intermediate pixel 1060. Subsequently, it may be associated with the pixel 870 by deflection by a different additional wedge (e.g. having the displacement h tan ψ) arranged in opposition (i.e. π phase shift angle) relative to the scanning wedge 710. One may note that in the illustrated embodiments this solution may result in relatively suboptimal compensation at least because the opposite curvatures of the circles 830 and 1070. Also, the practitioners may directly deduce that other approximative arrangements asymptotically approaching the illustrated solutions may be sufficient or even more desirable in practicing of different embodiments. Therefore, all such solutions are included herein, and may be considered as parts and/or variations of the instant invention.

The optimal phase shift angles ω and/or ξ may be found using directly from FIG. 10. Namely, straight forward trigonometry yields relationships $\omega=\phi+\sin^{-1}[(\sin \phi \tan \rho)/\tan \sigma]$ and $\xi=\pi+\phi-\sin^{-1}[(\sin \phi \tan \rho)/\tan \sigma]$. Also, as illustrated in FIG. 10 other depicted relationships between angles and radii may be readily calculated by practitioners.

The present invention has been described with references to the above exemplary embodiments. While specific values, relationships, materials and steps have been set forth for purpose of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

We claim:

1. A system for generation and adaptive implementation of overflying multi sensor measurements and derivation of actionable aggregants pertinent to determination of status and proactive management models of at least one distributed resource comprising:

at least one set of calibrated overflying multisensor detectors arranged for detecting signals from electromagnetic radiation redirected by a plurality of underlying structures having a combination of features having at least one scale length of interest;

at least one data processing computing device arranged for determination of a at least one set of overflight parameters and arranging and preprogramming the at least one set of overflying multisensor detectors for detecting and processing signals from electromagnetic radiation redirected by the plurality of underlying structures having the combination of features having the at least one scale length of interest;

an overflying apparatus arranged for enabling overflights and performing in-flight acquisition, preprocessing, and storing of data sets resulting from the multisensor measurements using the at least one set of overflying multisensor detectors;

at least one subsystem arranged for transferring the preprocessed data sets to at least one data analysis computing device arranged for analyzing the transferred data sets using the determined set of overflight parameters and a set of predetermined overflying multisensor detectors calibration data;

a subsystem for harmonization of the analyzed transferred data sets corresponding to the underlying structures, the features, the at least one scale length of interest and the actionable aggregants of interest; and determination of satisfactory consistency of the harmonized transferred data sets; and, in a case of unsatisfactory consistency of harmonized transferred data sets, determination of needs for additional data sets;

a subsystem arranged for adding the analyzed transferred data sets having satisfactory consistency into a database organized for storage and relational retrieval of data at least regarding the actionable aggregants, underlying structures, the features having the at least one scale length of interest, and time; and a subsystem arranged for obtaining external data pertinent to the actionable aggregants, underlying structures, the features having the at least one scale length of interest, and time and adding it relationally into the database;

wherein the at least one data analysis computing device have been arranged for determination of sufficiency of the analyzed transferred data sets for derivation of actionable aggregants pertinent to determination of status and proactive management of at least one distributed resource of interest, and, in a case of insufficient analyzed data sets, determination of needs for additional data sets.

2. The system of claim 1, wherein the at least one set of calibrated overflying multisensor detectors has been chosen from a group of detectors consisting of: visible, IR and UV spectrometers and spectro-photometers; visible, IR, and microwave radiometers, bolometers and spectrum analyzers, RADARs and Doppler RADARs; 2D and 3D LIDARs; and combinations of listed detectors.

3. The system of claim 2, wherein the at least one detector from the set of calibrated overflying multisensor detectors includes at least one imaging LIDAR.

4. The system of claim 3, wherein the at least one imaging LIDAR includes at least one directional scanner.

5. The system of claim 4, wherein the at least one directional scanner includes at least one point ahead correction system.

6. The system of claim 5, wherein the at least one directional scanner have been arranged to utilize a conical scan pattern.

7. The System of claim 6, wherein the at least one point ahead correction system incorporates at least one scanning optical wedge arranged to be rotated by an electromotor.

8. The system of claim 7, wherein the at least one point ahead correction system incorporates at least one compensator optical wedge arranged to be co-rotated with the at least one scanning optical wedge.

9. The system of claim 8, wherein the at least one compensator optical wedge has at least one opening arranged to pass through a transmitter photons with no deflection while correctively deflecting the incoming photons redirected from a scene under observation, and collected by the at least one imaging LIDAR.

10. The method of claim 9, wherein the at least one compensator optical wedge has been phase angle shifted with respect to the at least one scanning optical wedge, and performs point ahead correction when shifted with respect to the scanning optical wedge by a phase angle shift $\varphi+\pi/2$, wherein $-\pi/8 \leq \varphi \leq \pi/8$.

11. The method of claim 9, wherein the at least one compensator optical wedge has been phase angle shifted with respect to the at least one scanning optical wedge and performs the point ahead correction when shifted with respect to the at least one scanning optical wedge by a phase angle shift $\varphi+\pi/2$, such that substantially $\varphi=\phi/2$, wherein $\phi$ represents an angle of the at least one scanning optical wedge rotation during a time necessary of the transmitter photons to travel to and back from the scene under observation.

12. The system of claim 9, wherein the at least one point ahead correction system further incorporates at least one additional optical wedge arranged to be co-rotated with the at least one scanning optical wedge.

13. The system of claim 12, wherein the at least one additional optical wedge has at least one opening arranged to pass through a transmitter photons with no deflection while correctively deflecting the incoming photons redirected from a scene under observation, and collected by the at least one imaging LIDAR.

14. The system of claim 13, wherein the at least one compensator optical wedge has been phase angle shifted with respect to the at least one scanning optical wedge and performs the point ahead correction when shifted with respect to the at least one scanning optical wedge by a phase shift angle $\omega=\phi+\sin^{-1}[(\sin \phi \tan \rho)/\tan \sigma]$, wherein that $\phi$ represents an angle of the at least one scanning optical wedge rotation during a time necessary of the transmitter photons to travel to and back from the scene under observation, $\rho$ represents a deflection angle of the at least one scanning optical wedge and $\sigma$ represents a deflection angle of the at least one compensator optical wedge.

15. The system of claim 14, wherein the at least one additional optical wedge have been arrange with no shift relative to the at least one scanning optical wedge.

16. The system of claim 13, wherein the at least one compensator optical wedge has been phase angle shifted with respect to the at least one scanning optical wedge and performs the point ahead correction when shifted with respect to the scanning optical wedge by a phase shift angle $\xi=\pi+\phi-\sin^{-1}[(\sin \phi \tan \rho)/\tan \sigma]$, wherein that $\phi$ represents an angle of the at least one scanning optical wedge rotation during a time necessary of the transmitter photons to travel to and back from the scene under observation, $\rho$ represents a deflection angle of the at least one scanning optical wedge and $\sigma$ represents a deflection angle of the at least one compensator optical wedge.

17. The system of claim 16, wherein the at least one additional optical wedge have been arrange in opposition to the at least one optical wedge with shift of $\pi$ relative to the at least one scanning optical wedge.

* * * * *